United States Patent [19]
Partridge

[11] 4,077,413
[45] Mar. 7, 1978

[54] DEFIBRILLATOR

[75] Inventor: Leslie W. Partridge, Janesville, Wis.

[73] Assignee: The Burdick Corporation, Milton, Wis.

[21] Appl. No.: 683,016

[22] Filed: May 4, 1976

[51] Int. Cl.² .............................................. A61N 1/36
[52] U.S. Cl. .................................. 128/419 D; 363/37
[58] Field of Search .................. 128/419 D, 421, 422, 128/423; 331/112, 148; 321/2

[56] References Cited

U.S. PATENT DOCUMENTS

| 3,258,013 | 6/1966 | Druz | 128/419 D |
| 3,389,704 | 6/1968 | Buchowski et al. | 128/419 D |
| 3,513,850 | 5/1970 | Weber | 128/419 D X |
| 3,547,108 | 12/1970 | Seiffert | 128/419 D X |
| 3,653,387 | 4/1972 | Ceier | 128/419 D X |
| 3,814,105 | 6/1974 | Howard et al. | 128/419 D |
| 3,828,239 | 8/1974 | Nagai et al. | 321/2 |
| 3,860,009 | 1/1975 | Bell et al. | 128/419 D |
| 3,863,125 | 1/1975 | Tollrian et al. | 321/2 X |
| 3,925,717 | 12/1975 | Kinnard | 321/2 |

FOREIGN PATENT DOCUMENTS 864,362  4/1961  United Kingdom ........... 128/419 D

Primary Examiner—William E. Kamm
Attorney, Agent, or Firm—Mason, Kolehmainen, Rathburn & Wyss

[57] ABSTRACT

An improved automatic defibrillator operable from an internal rechargable battery power source or from an A.C. line when the battery is discharged utilizes a high efficiency flyback type power supply for charging the energy storage capacitor. The capacitor charging power supply employs an isolated output thereby allowing the defibrillator electrodes to be switched between the storage capacitor and an electrocardiogram unit by the discharge relay and avoiding the need for a separate relay or isolating impedance to isolate the pre-amplifier of the electrocardiogram unit from the defibrillator circuit. Finally automatic circuitry is employed to control the battery power supply so that the number of watt seconds (Joules) of energy delivered by the defibrillator may be easily selected by a single selector switch, and the charging of the capacitor terminated when the energy necessary to deliver the amount of energy selected has been stored.

32 Claims, 5 Drawing Figures

DEFIBRILLATOR

BACKGROUND OF THE INVENTION

A. Field of the Invention

This invention relates generally to defibrillator circuits, and more particularly to portable, automatic defibrillators that may be operated from an internal battery when no A.C. power source is available, and which may be operated directly from the A.C. power source even though the internal battery may be discharged.

B. Description of the Prior Art

Defibrillator circuits for applying an electrical shock to a patient undergoing the rapid irregular contractions of the muscle fibers of the heart known as fibrillation. The prior art devices used to administer such an electrical shock typically consisted of a storage capacitor that was charged to a relatively high potential by a D.C. power supply and discharged into the patient through the series combination of an inductor and a relay.

The early prior art devices were designed to operate from an A.C. power source, and the amount of charge accumulated on the capacitor prior to discharge was adjusted by adjusting the output voltage of the power supply by means of a variable voltage transformer or the like. The amount of charge accumulated by the storage capacitor was determined by measuring the voltage across the capacitor by means of a voltmeter or the like and adjusting the variable voltage transformer until the desired reading is obtained. The capacitor was then discharged into the patient by closing the relay contacts.

Other prior art defibrillators were designed to be used as portable units in an ambulance or in other environments where a source of A.C. power was not available. These units typically utilized a battery such as a rechargable nickel cadmium battery as the power source and incorporated a small line current powered power source for charging the battery. Both the line powered units and the battery powered units had provisions for connecting the defibrillator electrodes to a preamplifier so that an electrocardiogram could be taken utilizing the defibrillator electrodes.

While these units did provide a way to defibrillate a stricken patient, the units were relatively cumbersome and difficult to operate, and could be dangerous if improperly used. Furthermore, the A.C. line powered units could not be used when a source of alternating current was unavailable, and the battery operated units could not be used if the battery was discharged, since, in order to achieve lightness and portability, the power supply in the battery power units was designed only as a battery charging system and did not have sufficient capacity to operate the unit without the aid of the battery. All of these units required large amounts of power to operate them. Moreover, when the electrodes of the defibrillator were also used as sensing electrodes for the electrocardiogram, a separate relay or other isolation device, such as a resistor had to be placed between the electrocardiogram unit and the defibrillator electrodes to prevent the defibrillator discharge from damaging the electrocardiogram unit. The use of a separate relay increased the complexity of the unit and damage to the electrocardiogram unit could occur should the isolating relay fail. The use of a high impedance coupling between the electrocardiogram unit and the defibrallator electrodes attenuated the electrocardiogram signal and caused noise and interference to be picked up by the electrocardiogram. Consequently, shielded cables had to be used to connect the electrocardiogram units to the electrodes to reduce the noise pickup; however, the capacitance of the cable increased the leakage current between the chassis and the electrodes.

Finally, the prior art units had no way of automatically charging the storage capacitor to a preselected watt second level, and were inefficient in the use of power. The inefficiency became a particular problem in battery powered units.

SUMMARY OF THE INVENTION

Accordingly, it is an object of the present invention to provide an improved defibrillator that overcomes many of the disadvantages of the prior art circuits.

It is another object of the present invention to provide an improved defibrillator that can be operated from an internal battery source when no A.C. power is available, and which can be operated from an A.C. line even if the internal battery is discharged.

It is another object of the present invention to provide an improved defibrillator that is efficient in the use of electrical power.

It is yet another object of the present invention to provide a defibrillator that may be more easily operated and controlled.

It is still another object of the present invention to provide a defibrillator that has automatic control circuitry for charging the storage capacitor to a level corresponding to an energy level that may be preselected by the operator means of a single control switch.

It is another object of the present invention to provide a defibrillator utilizing only a single relay to switch the defibrillator electrodes between the defibrillator output and the electrocardiogram input.

It is another object of the present invention to provide a light weight portable defibrillator having greater output power and requiring substantially less input power than the prior art units.

It is yet another object of the present invention to provide an improved defibrillator that is safer to operate than the prior art units.

In accordance with a preferred embodiment of the invention, the defibrillator according to the invention employs a compact high efficiency switching power supply that is operable from an A.C. line and used to charge a storage battery, such as a nickel cadmium battery. The switching power supply is also capable of driving the defibrillator circuitry directly even when the storage battery is discharged so that the defibrillator may at all times be operated from any available power source regardless of the state of charge of the battery.

A high efficiency flyback type of power source powered by either the storage battery or the switching power supply is used to charge a storage capacitor which is subsequently discharged into the patient during defibrillation. The flyback power supply, which is particularly suitable for charging a capacitor since it minimizes resistive losses and provides an output power that is substantially independent of the state of charge of the capacitor, utilizes a step up transformer having a low voltage primary, a high voltage secondary for charging the storage capacitor and a tertiary winding. The tertiary winding is coupled to logic circuitry within the defibrillator that senses the amplitude of the voltage spikes developed across the tertiary winding and automatically turns off the flyback power supply when the spikes reach a preselected amplitude determined by the setting of an energy selector switch. This permits the level of charge on the storage capacitor to be sensed without making a direct connection to the capacitor, and prevents the storage capacitor from being slowly discharged by the level sensing circuitry. An indicator light and an audible alarm are automatically energized when the storage capacitor reaches the preselected charge.

The high voltage secondary winding of the transformer employed in the flyback power supply is fully isolated from ground, thereby permitting a single relay to be used to connect the defibrillator electrodes either to the storage capacitor or to the preamplifier of an electrocardiogram unit without the use of any additional isolating circuitry between the defibrillator output and the preamplifier input. This is accomplished by leaving the storage capacitor connected to the isolated output winding of the flyback transformer at all times, and utilizing the relay normally used to disconnect the capacitor from the secondary winding for switching the defibrillator electrodes between the preamplifier input and the storage capacitor while the capacitor remains connected to the isolated secondary winding of the flyback transformer.

Finally, in order to increase the operating safety of the defibrillator, circuitry is provided within the logic circuit for automatically discharging the storage capacitor if the setting of the energy selector switch is reduced after the storage capacitor has been previously charged to a higher level in order to prevent a large charge from being inadvertantly applied to the patient. In addition, the logic circuit is provided with circuitry for preventing the patient from being defibrillated while the flyback power supply is operating. Sensing circuits that automatically discharge the storage capacitor upon the malfunction of a critical component are also provided. In addition, a separate defibrillation switch is mounted on each of the defibrillator electrodes, and both switches must simultaneously be closed in order to discharge the capacitor, thereby reducing the probability of and inadvertant discharge that could cause a hazardous electrical shock.

DESCRIPTION OF THE DRAWINGS

The above and other objects and advantages of the present invention will be more readily understood with reference to the following specification and attached drawings wherein.

DETAILED DESCRIPTION OF THE PREFERRED EMBODIMENT

Figure 1:
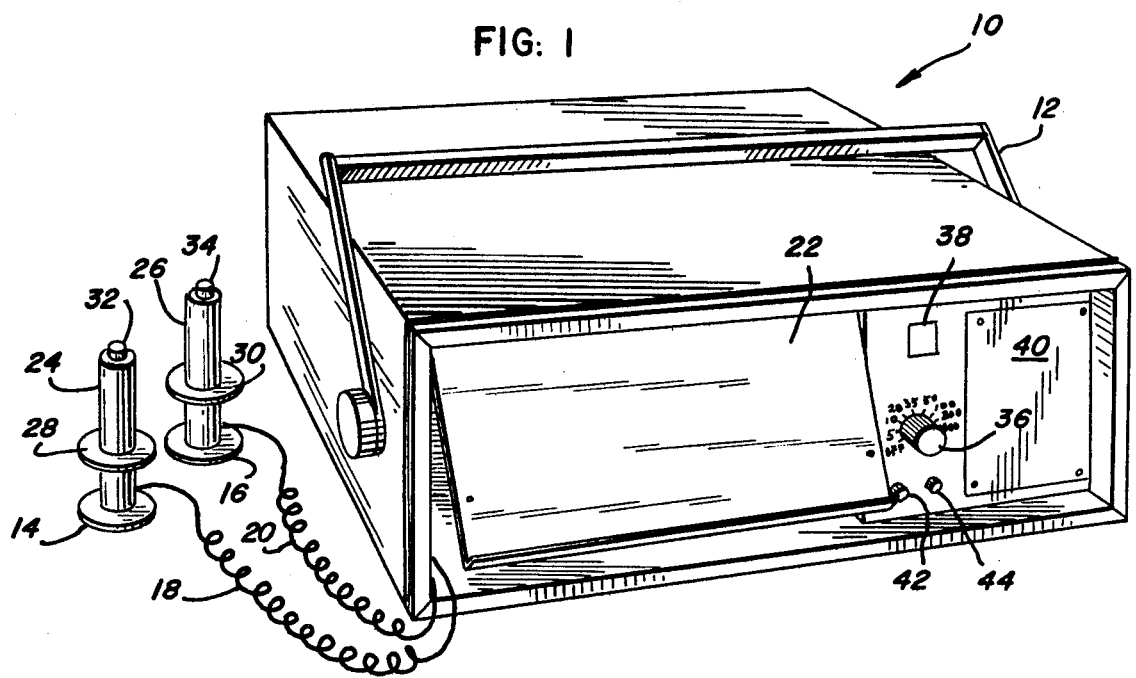
FIG. 1 is a perspective view of the defibrillator according to the invention.

Referring now to the drawings, with particular attention to FIG. 1, there is shown a defibrillator generally designated by the reference numeral 10. A carrying handle 12 is affixed to the defibrillator 10, since, due to its compact and light weight design, the defibrillator is well suited for portable applications. A pair of defibrillating electrodes 14 and 16 (sometimes known as paddles) are connected to the defibrillator 12 by a pair of respective cables 18 and 20. The electrodes 14 and 16 and the cables 18 and 20 may be stored in a compartment (not shown) behind a door 22 (shown partially open) forming part of the front panel of the defibrillator 10. A pair of handles 24 and 26 are attached to the respective electrodes 14 and 16, and a pair of insulated stop plates 28 and 30 are disposed about the respective handles 24 and 26 to maintain the hands of an operator at a safe distance from the electrodes 14 and 16. A pair of push-button switches 32 and 34 are disposed on top of the respective handles 24 and 26. These push-button switches 32 and 34 must be depressed simultaneously to deliver the defibrillation energy to the patient.

In accordance with an important aspect of the invention, logic circuitry is provided within the defibrillator 10 for automatically controlling the amount of energy to be delivered to the patient. The logic circuitry is controlled by a multiposition energy selector switch 36 mounted on the front panel of the defibrillator 10 and used to select an appropriate amount of defibrillation energy comensurate with the size of the patient and the severity of his condition. A charge initiating switch 38 is also mounted in the front panel of the defibrillator unit 10 and is used to initiate the charging of a storage capacitor within the unit 10 after the desired of energy has been selected by the selector switch 36. A light behind the push-button of the switch 38 and an audible signal generator (not shown in FIG. 1) are energized after the storage capacitor has been charged to the level selected by the selector switch 36 indicating that the unit is now ready to be operated. Finally, the unit 10 is designed to accomodate an optional preamplifier that may be used in conjunction with an electrocardiogram unit or a synchronizer mounted behind a blank panel 40. A power-on indicator 42 and a low battery indicator 44 are also provided.

Figure 3:
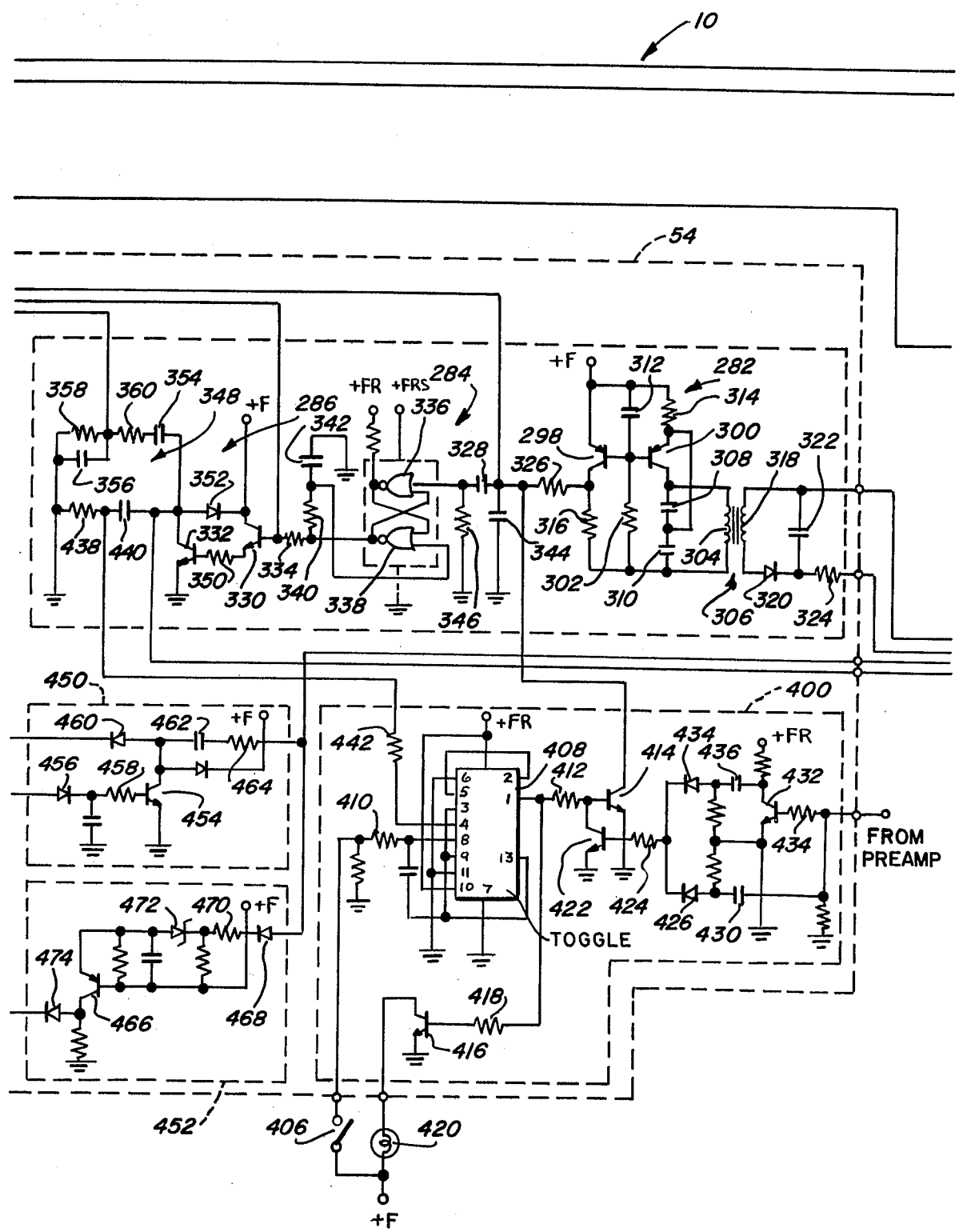
Figure 4:
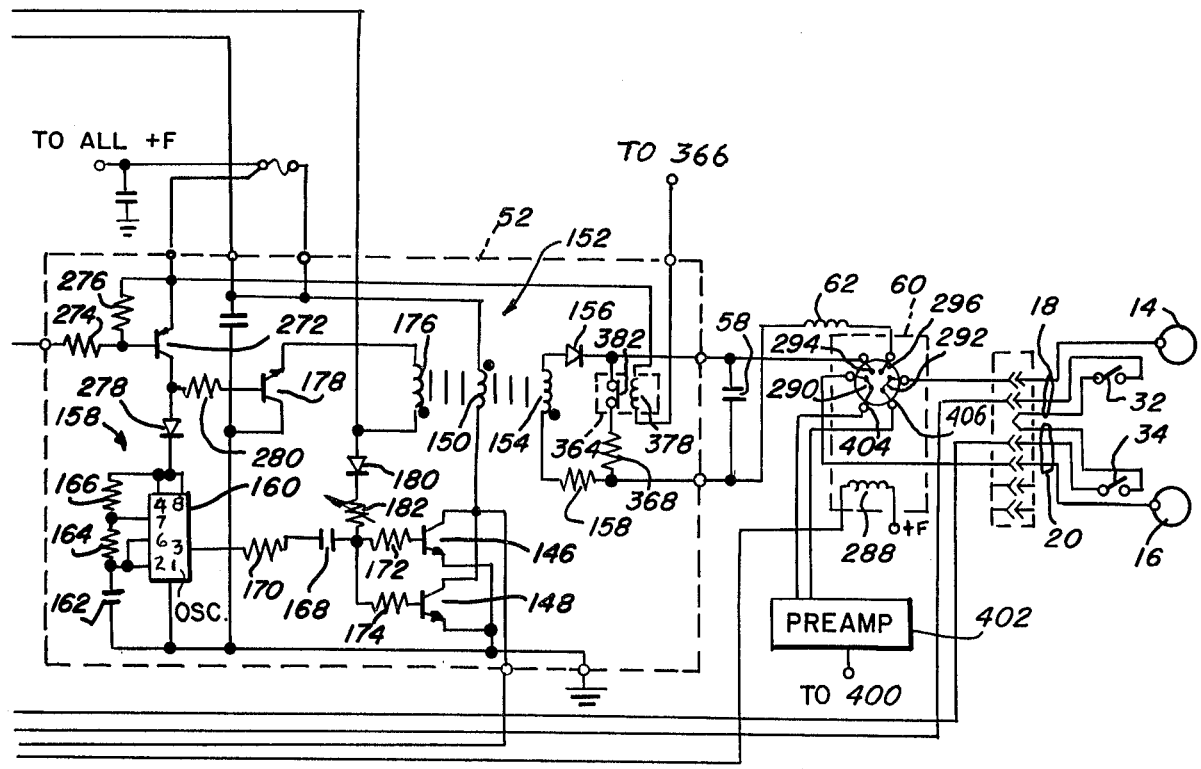
Figure 4:
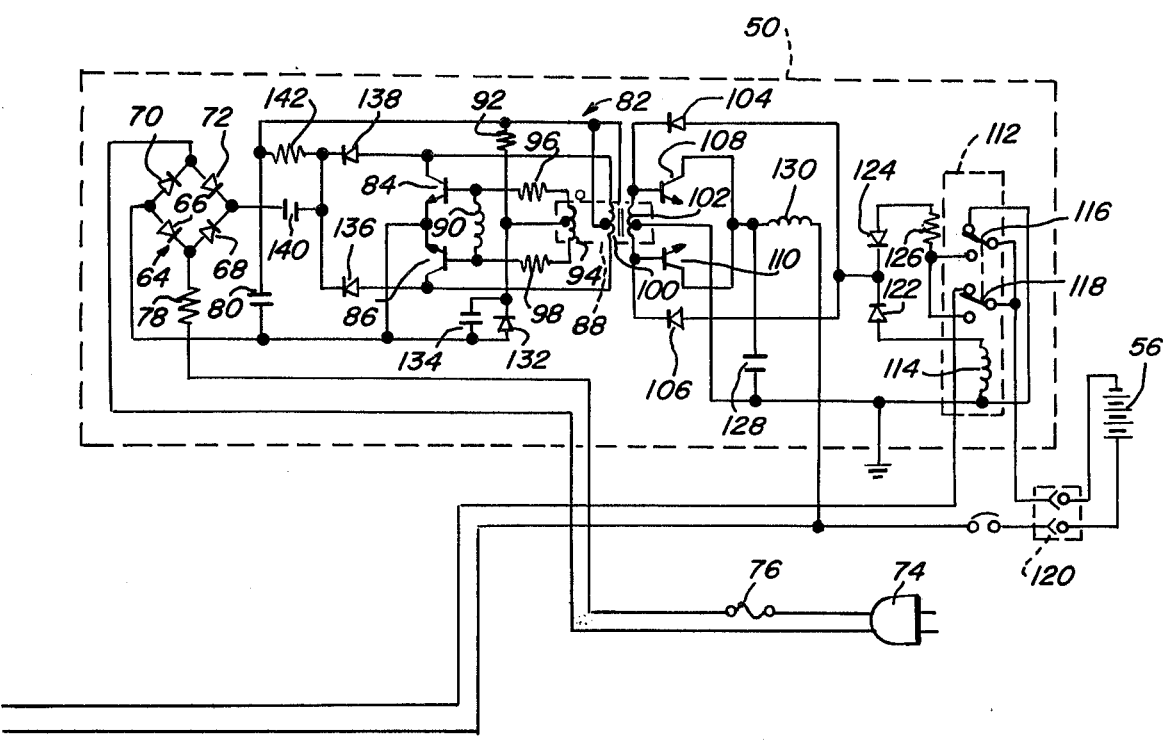

The circuit of the defibrillator 10 contains a switching power supply, generally designated by the reference numeral 50 (FIG. 4), a high voltage flyback type power supply 52 and a logic circuit 54 (FIG. 3). The switching power supply 50 serves to convert A.C. line current to a relatively low voltage direct current suitable for charging a rechargable storage battery 56 and for operating the defibrillator circuitry directly when a source of A.C. line current is available.

The high voltage flyback power supply 52 receives the direct current power provided by either the battery 56 or the switching power supply 50 and converts it to a relatively high voltage (on the order of several kilovolts) direct current for charging a storage capacitor 58. The logic circuit 54 controls the level of charge applied to the capacitor 58. The logic circuit 54 also controls a defibrillate relay 60 that connects the capacitor 58 to the electrodes 14 and 16 through an inductor 62 in order to discharge the capacitor 58 through the electrodes 14 and 16 upon command from the logic circuit 54 when the push-buttons 32 and 34 are depressed. Other functions relating to safety and ease of operation are also provided by the logic circuit 54 and will be discussed in a subsequent portion of the specification.

More specifically, the switching power supply 50 contains a full-wave rectifier bridge 64 containing four diodes 66, 68, 70 and 72 that receive alternating current power from a power line via a plug 74 and a line fuse 76. A resistor 78 is connected in series with the power line to limit the maximum current that may be drawn by the bridge. The line current is rectified by the bridge 64 and filtered by a filter capacitor 80. The rectified and filtered current is applied to an inverter circuit 82 comprising a pair of switching transistors 84 and 86, a step down transformer 88, a saturable reactor 90 and other associated components.

When line current is first applied to the rectifier bridge 64, a forward biasing potential is applied to the transistors 84 and 86 through a resistor 92, a feedback winding 94 of the transformer 88 and a pair of resistors 96 and 98. Since no two transistors are exactly alike, one of the transistors 84 and 86 will conduct slightly before the other and cause current to flow through one half of a center tapped primary winding 100 of the transformer 88. The windings 94 and 100 are wound in a direction such that when one of the transistors conducts, for example, transistor 84, the voltage induced in the feedback winding 94 will have the polarity required to maintain that transistor (transistor 84) conductive, thereby causing gradual build-up of current through the appropriate path of the winding 100. In the present example, with the transistor 84 being conductive, current will flow from the junction of the diodes 68 and 72, through the center tap of the winding 100, through the collector and emitter electrodes of the transistor 84 and back to the junction of the diodes 64 and 70.

In a conventional switching power supply, the current through the appropriate path of the winding 100 would continue to build until the core of the transformer 88 became saturated. At this point, the magnetic flux in the core would cease to increase, and the voltage induced in the feedback winding 94 would be insufficient to maintain the transistor 84 fully conductive. Consequently, the transistor 84 would tend to become less conductive and cause a reduction in the amount of current flowing through the transistor 84 into the winding 100. This reduction in current would cause a reduction in the magnetic flux in the core of the transformer 100, thereby reversing the polarity of the voltage induced in the feedback winding 94. This polarity reversal would rapidly turn the transistor 84 off and render the transistor 86 conductive. Upon being rendered conductive, the transistor 86 would complete a current path from the junction of the transistors 68 and 72 through the previously unenergized half of the winding 100, through the transistor 86 and to the junction of the transistors 64 and 70. This current flow would induce a voltage in the feedback winding 94 to maintain the transistor 86 conductive until the core of the transformer 88 again saturated, at which point the cycle would be repeated with the transistor 84 being rendered conductive and the transistor 86 being rendered nonconductive.

One of the problems with conventional power supplies of the type described in the foregoing paragraph wherein the core of the transformer 88 saturates prior to the switching operation is that during the time that the core is saturated, large amounts of current are drawn through the primary winding. thereby resulting in a heating of the transformer 88 and other components and a waste of power.

Accordingly, in accordance with an important aspect of the present invention, the saturable reactor 90 is connected across the feedback winding 94 of the transformer 88. The saturable reactor 90 is designed so that it saturates before the transformer 88 saturates, and thereby initiates the switching of the transistors 84 and 86 prior to the saturation of the core of the transformer 88. For example, as in the example previously discussed, when the transistor 84 is rendered conductive, a voltage tending to maintain the transistor 84 conductive is induced in the feedback winding 94. With the saturable reactor 90 connected across the winding 84, the voltage induced in the winding 94 causes a gradually increasing current to flow through the saturable reactor 90. When this gradually increasing current reaches a level sufficient to saturate the saturable reactor 90, the reactance of the saturable reactor will drop. This drop in reactance will cause a greater proportion of the current from the winding 94 to flow through the reactor 90 and a lesser proportion to flow through the base of the transistor 84 until the drive to the transistor 84 is sufficiently reduced so that the current flowing through the transistor 84 cannot be maintained. At this point, the current flowing through the transistor 84 and the winding 110 will be reduced, thereby causing a reversal in the polarity of the voltage induced in the winding 94. This reversal renders the transistor 84 nonconductive and the transistor 86 conductive and results in switching action. Since the current flowing in the base circuits of the transistors 84 and 86 is substantially lower than the current flowing through the collector circuits, only a fraction of the power previously dissipated is dissipated in the saturable reactor 90, thereby resulting in much more efficient operation of the switching power supply. Furthermore, the saturable reactor 90 provides a convenient way to control the switching frequency of the switching power supply, because the frequency can be readily altered simply by changing the value of the saturable reactor 90.

The alternating flow of current through the two halves of the primary winding 100 induces a voltage in a secondary winding 102 of the transformer 88. This induced voltage is rectified by two separate rectifying circuits, the first consisting of a pair of diodes 104 and 106, and the second consisting of a pair of transistors 108 and 110. In this embodiment the base to collector junctions of the transistors 108 and 110 are used as rectifying diodes, and the emitters are not used. The diodes 104 and 106 provide a negative direct current potential for charging the battery 56 and the rectifying transistors 108 and 110 provide a positive direct current potential for operating the defibrillator unit.

Also included in the power supply circuit 50 is a relay 112 having a coil 114 that operates a pair of double throw switches 116 and 118. With the relay coil 114 deenergized, and the switches 116 and 118 positioned as shown, the battery 56 is connected (via a connector 120) through the switches 116 and 118 to the defibrillator circuit 10 and the unit is conditioned to operate from battery power. When the plug 74 is inserted into a source of alternating current potential, the coil 114 of the relay 112 is energized through a diode 122 by the negative potential appearing at the junction of the anodes of the diodes 104 and 106. This actuates the switches 116 and 118 to the opposite position and causes the battery 56 to be connected to the charging potential source through a diode 124 and a current limiting resistor 126. In this embodiment, the switches 116 and 118 are connected in parallel for greater current handling capacity. In this condition, the defibrillator 10 is being powered by the positive potential developed by the transistors 108 and 110 and filtered by a filtering network including a capacitor, shown next to transistor 272, and an inductor 130.

A diode 132 and a capacitor 134 complete the current path between the center tap of the feedback winding 94 and the junction of the diodes 64 and 70, and the diodes 136 and 138, together with a capacitor 140 and a resistor 42, form a snubber circuit to eliminate high voltage transients that may be generated by the switching process. The diodes 122 and 124 are used to isolate the battery 56 from the relay coil 114 to prevent the relay from "latching up" when the relay has been pulled in.

Power from the switching power supply 50 or the battery 56 is applied to the flyback type high voltage power supply through an on/off switch 144 that is ganged with the energy selector switch 36. The flyback type power supply includes a pair of switching transistors 146 and 148, connected in parallel for greater current carrying capacity, driving a primary winding 150 of a high voltage transformer 152. A completely isolated or floating secondary winding 154 of high voltage transformer 152 charges the storage capacitor 58 through a rectifier diode 156 and a resistor 158.

The transistors 146 and 148 are driven by an oscillator circuit 158 including an integrated circuit chip 160, a capacitor 162 and resistors 164 and 166. In the present embodiment, the integrated circuit chip 160 is an NE555V timer manufactured by Signetics, Inc. of Sunnyvale, Calif.; however, any suitable oscillator circuit may be used. The output of the oscillator circuit 158 serves to render the transistors 146 and 148 periodically conductive by applying pulses to the bases thereof through a capacitor 168 and resistors 170, 172 and 174.

When the transistors 146 and 148 are rendered conductive, current flows from either the power supply 50 or the battery 56 through the switch 144 into the primary of the flyback transformer 152 and through the transistors 146 and 148 to ground. As the transistors 146 and 148 remain conductive, current gradually builds in the primary winding 150 thereby inducing a voltage in the feedback winding 176 of the proper polarity to maintain the transistors 146 and 148 conductive. A control transistor 178, normally conductive when the flyback power supply is operating, and a diode 180 and a variable resistor 182 complete the current path between the winding 176 and the bases of the transistors 146 and 148.

As the current through the primary 150 reaches a value corresponding to the maximum current that can be delivered by the transistors 146 and 148 under the drive conditions provided, the forward biasing drive current supplied by the winding 176 is reduced, thereby reducing the current applied to the primary 150. This reduction in current causes a reverse biasing voltage to be induced in the winding 176, thereby rapidly turning off the transistors 146 and 148. The rapid turn-off of the transistors 146 and 148 results in a voltage spike appearing across the primary 150 as the inductance of the transformer attempts to maintain the previously attained current flowing through the primary 150. This voltage spike is transformed by the secondary winding 154 to a much higher voltage level (on the order of several kilovolts), and is rectified so that it may be used to charge the storage capacitor 58.

Because the value of the power from the secondary winding 154 is dependent primarily on the peak value of the current through the primary 150 prior to switching and not on the state of charge of the capacitor 58, the charging power rate of the capacitor does not drop as the capacitor 58 is charged, thereby providing a more rapid charging of the capacitor 58 as well as the increased efficiency characteristic of switching type power supplies. Furthermore, because of transformer coupling, the amplitude of the high voltage spike thus generated is dependent on the state charge of the capacitor 58. When the capacitor 58 is fully discharged, it behaves as a low impedance device and thereby limits the amplitude of the resultant voltage spikes. As the capacitor 58 charges, the amplitudes of the voltage spikes gradually increase proportionately to the voltage across the capacitor 58. A reduced amplitude replica of this variable amplitude spike waveform also appears across the winding 176 and provides a convenient way for determining the state of charge of the capacitor 58 without making a direct connection to the capacitor 58. This is advantageous since direct connections to the capacitor 58 tend to bleed off the charge from the capacitor 58. In addition, if sensing circuitry were connected directly across the capacitor 58 such sensing circuitry would have to withstand the high voltages present at the capacitor 58.

Therefore, in accordance with another important aspect of the present invention, the waveform appearing across the winding 176 is applied to the logic circuitry 54 via the energy selector switch 36 and compared with a reference within the logic circuit 54. When the amplitude of the waveform from the winding 176 exceeds the references, the logic circuit 54 automatically terminates the charging of the capacitor.

More specifically, a resistive network 185 comprising resistors 184, 186, 188, 190, 192, 194, 196, 198, 200, 202, and 204 is connected to the energy selector switch 36. The voltage waveform from the winding 176 is either passed directly through the switch 36 or through a portion of the resistive network 185, depending on the position switch 36. When a low energy (watt second) setting is desired, the waveform is passed through low valve resistors. As increasing levels of energy are selected, the waveform is passed through correspondingly higher values of resistance within the resistance network 185. Consequently when a higher value of energy is selected, the capacitor 158 must be charged to a higher value before the more highly attenuated waveform from the winding 176 applied to the logic circuit 54 exceeds the predetermined reference.

The predetermined reference is determined by a double regulator circuit comprising a pair of Zener diodes 206 and 208, resistors 210 and 212 and associated circuitry. The Zener diodes 206 and 208 establish a constant voltage at the junction of the Zener diode 208 and the resistor 212. This in turn determines the current that will flow through a resistor 214 and a variable resistor 216.

The spikes applied to the switch 36 from the winding 176 are applied to the base of a transistor 218. The spikes are negative going spikes and the transistor 218 is a PNP transistor, so the spikes tend to turn on the transistor 218. However, the polarity of the reference source is such that it tends to keep the transistor 218 turned off. Consequently, the transistor 218 is normally in a nonconductive state until the amplitude of the spikes generated by the winding 216 reaches a sufficiently high amplitude so that the current flowing through the energy selector switch 36 exceeds the current that can be supplied through the resistors 214 and 216. At this point, the excess current available from the winding 176 can be applied to the base of the transistor 218 to render the transistor 218 conductive.

The transistor 218 has a resistor 220 connected in its emitter circuit and operates as an emitter follower to drive a transistor 222, while a capacitor 219 in the base circuit of the transistor 218 prevents the transistor 218 from being turned off prematurely by unwanted spikes. The transistor 222 serves as a common emitter amplifier to drive one input of a bistable multivibrator 226. The multivibrator 226 comprises a pair of cross coupled NOR gates 228 and 230.

The transistor 222 is normally conductive, and a low state signal is applied to the input of the NOR gate 230, thereby resulting in a low state output from the gate 228. When the capacitor 58 reaches the desired charge, the transistor 218 is rendered conductive, thereby rendering the transistor 222 nonconductive and applying a high state signal to the gate 230. This results in a high state signal at the output of the gate 228 which is used to drive a transistor 232 (via a diode 234 and a resistor 236) and an oscillator 240 via a diode and a resistor 244. The output of the transistor 232 is used to energize a ready light 246 in order to indicate that the unit has reached the desired energy. The oscillator 240 is used to activate an audible signal source such as a loud speaker 248. In this embodiment, the oscillator 240 comprises an integrated circuit chip 250 similar to the integrated circuit chip 160 and associated resistors 252, 254 and 256, and a capacitor 258, however, any suitable oscillator may be used.

The bistable multivibrator 226 drives a second bistable multivibrator 260 comprising a pair of cross coupled gates 262 and 264. The output of the gate 262 reaches a low state at the same time that the ready light and audible signal source 248 are energized. This low state is coupled to a transistor 266 through a resistive network comprising resistors 268 and 270 and renders the transistor 266 nonconductive. The output of the transistor 266 is coupled to a transistor 272 (FIG. 4) though a resistive network comprising resistors 274 and 276, and, in turn renders the transistor 272 nonconductive. The rendering nonconductive of the transistor 272 disables the oscillator 158, which has been receiving power through the transistor 272 and a diode 278. Simultaneously the rendering nonconductive of the transistor 272 renders the transistor 178, which had been receiving base drive from the transistor 272 through a resistor 280, nonconductive. As a result, the oscillation sustaining feedback loop from the winding 176 to the bases of the transistors 146 and 148 is opened, and the operation of the flyback power supply is terminated. Since the oscillator 158 is also disabled by the rendering nonconductive of the transistor 272, the supply will not be restarted until the transistor 272 is again rendered conductive. At this point, the storage capacitor 58 is ready to be discharged into the patient.

The discharging is accomplished by simultaneously closing the switches 32 and 34 associated with the respective electrodes 14 and 16. The closing of the switches 32 and 34 places a low impedance load across the output of an oscillator 282 in the logic circuit 54 and causes the oscillator 282 (FIG. 3) to apply a triggering signal to a monostable multivibrator 284 which in turn operates a defibrillator driver circuit 286. The defibrillator driver circuit 286 energizes a winding 288 in the defibrillation relay 60 (FIG. 4) thereby causing a pair of armatures 290 and 292 to make contact with a pair of respective normally open contacts 294 and 296 to connect the storage capacitor 58 to the electrodes 14 and 16.

More specifically, the oscillator circuit 282 (FIG. 3) comprises a pair of transistors 298 and 300 and associated circuitry. A resistor 302 tends to forward bias both of the transistors 298 and 300, and a tuned circuit comprising a primary winding 304 of an isolating transformer 306 and a pair of capacitors 308 and 310 determine the frequency of oscillation of the oscillator 282. Oscillation sustaining feedback occurs between the junction of the capacitors 308 and 310 and the emitter of the transistor 300. A capacitor 312 serves as a base bypass capacitor for the transistors 298 and 300, a resistor 314 serves as an emitter load for the transistor 300 and a resistor 316 serves as a collector load for the transistor 298.

The transformer 306 has a secondary winding 318 that is connected to a rectifying and filtering circuit comprising a diode 320 and a capacitor 322. Under normal operation conditions the diode 320 and capacitor 322 serve as a very light load for the oscillator 282, thereby permitting oscillation to be maintained. When the switches 32 and 34 are closed, a low value resistor 324 is connected across the capacitor 322 thereby loading down the secondary winding 318 of the transformer 306 a sufficient amount to terminate or reduce the oscillation of the oscillator 282. When oscillation is terminated, the transistor 298 is rendered conductive by the biasing resistor 302 and applies a positive potential pulse to the monostable multivibrator 284 through a resistor 326 and a capacitor 328. In this manner, the oscillator 282 generates a D.C. voltage change in response to the closing of the switches 32 and 32 while maintaining complete direct current isolation between the switches 32 and 34 and the rest of the defibrillator circuit through the transformer 306.

The increasing voltage from the output of the transistor 298 triggers the monostable multivibrator 284 and causes the multivibrator 284 to apply a positive going pulse having approximately a 50 millisecond duration to a pair of direct current coupled transistors 330 and 332 through a resistor 334. In the present embodiment, the monostable multivibrator 84 is an integrating monostable comprising a pair of cross coupled NOR gates 336 and 338 and a timing network comprising a resistor 340 and a capacitor 342. An integrating type of monostable is used rather than a differentiating type to increase noise immunity, since the capacitor 342 in the feedback loop tends to filter out undesired transients. Similarly, a capacitor 344 in the input line to the gate 336 also tends to filter out transients, and a resistor 346 biases the input to the NOR gate 336 at a low level absent any input signal.

The pulse from the monostable multivibrator 284 is inverted and applied to a pulse shaping circuit 248 by the transistors 330 and 332 which are coupled by a resistor 350. Diode 352 is a transient supressor for relay coil 288. The output of the transistor 332 drives the coil 288 of the defibrillating relay 60. In addition, the negative going pulse is differentiated by a network comprising a pair of capacitors 354 and 356, and a pair of resistors 358 and 360, in order to obtain a positive pulse at the end of the defibrillate cycle. This pulse is then applied to a bistacle multivibrator 362 which drives a disarming relay 364 via a driver transistor 366. This causes the disarming relay 364 to connect a load 368 across the capacitor 358 approximately 50 milliseconds after the defibrillating relay 60 was energized. This assures that the capacitor 58 is completely discharged after the defibrillation process and prevents a potentially dangerous electrical shock to the operating personnel in the event that the capacitor 58 has not been completely discharged.

The bistable multivibrator 362 is utilized to initiate the next charging cycle. The charging cycle is initiated by closing the switch 38 which applies a positive pulse to the gate 370 of the bistable multivibrator 362 via a resistor 390 and a network comprising a capacitor 384 and a pair of resistors 386 and 388. The positive pulse applied to the gate 370 causes the gate 372 to apply a positive output to the transistor 366, thereby connecting one end of the relay coil 378 to ground and energizing the disarming relay. This causes the contacts 382 to open and removes the low impedance load from the capacitor 58. Simultaneously, the positive output from the gate 372 is applied to the gate 264 of the bistable multivibrator 260 through a capacitor 392. This causes the gate 262 to render the transistor 266 conductive thereby rendering the oscillator circuit 158 operative and rendering the transistor 178 conductive to close the feedback loop between the winding 176 and the transistors 146 and 148. This initiates the operation of the power supply 52 and permits the power supply 52 to charge the capacitor 58.

The bistable multivibrator 362 contains a pair of cross coupled NOR gates 370 and 372. Upon receipt by the gate 372 (via a resistor 374) of the positive going pulse from the network 348, the output of the gate 372 goes low. This low level output is applied to the transistor 366 through a resistor 376 thereby rendering the transistor 366 nonconductive. When the transistor 366 is rendered nonconductive, both sides of a coil 378 are connected to a positive source of potential, one through a diode 380 and the other directly. Since both sides of the coil 378 are now at the same potential, the coil is deenergized, and a pair of normally closed contacts 382 connect the load 368 across the capacitor 58.

The electrodes 14 and 16 need not be used only for defibrillation purposes, but may also be used to drive an electrocardiogram unit or a synchronizing unit such as a synchronizing unit 400 within the logic circuit 54. When this is done, the electrodes 14 and 16 must be connected to a preamplifier 402, such as, for example, the model DC-175 preamplifier manufactured by the Burdick Corporation of Milton, Wisconsin.

In accordance with an important aspect of the present invention, the electrodes 14 and 16 are selectively connected to the preamplifier 402 by the defibrillating relay 60. This can be accomplished only because the output winding 154 of the flyback power supply 52 is completely isolated from ground, thereby eliminating the necessity for disconnecting the capacitor 58 from the winding 154 during defibrillation. Consequently, the electrodes 14 and 16 may be connected to the armatures 290 and 292 of the relay 60, and the preamplifier 402 may be connected to a pair of normally closed contacts 404 ad 406 within the relay 60. When defibrillation occurs, the electrodes 14 and 16 are connected to the capacitor 58 through the normally open contacts 294 and 296, and are completely isolated from the preamplifier 402.

The output of the preamplifier 402 is connected to the synchronizer 400 to permit the defibrillation discharge to be delivered to the patient in synchronism with the patient's own cardiac wave (R-wave). This is accomplished by the synchronizing unit 400 which senses the patient's amplified cardiac wave provided by the amplifier 402, and inhibits the discharging of the storage capacitor into the patient until an R-wave occurs.

The operation of the synchronizer circuit 400 is initiated by momentarily closing a switch 406. This momentary pulse is transferred to an integrated circuit 408 via a resistor 410. In the present embodiment, the integrated circuit 408 is a CD4013AE dual D-type flip-flop manufactured by RCA Solid State Division, Somerville, N.J.; however, any circuit that alternately provides a high and low output each time the switch 406 is momentarily closed to convert a momentary action to a toggle action may be used.

After the switch 406 has momentarily closed, the high signal from the circuit 408 is applied through a resistor 412 to a transistor 414. The transistor 414 is rendered conductive and brings the junction of the resistor 326 and capacitor 328 close to ground potential. This prevents the high level signal from the transistor 298 that occurs when the defibrillate switches 32 and 34 are closed from triggering the monostable multivibrator 284, and prevents the storage capacitor 58 from being discharged. In addition, the high level signal drives a second transistor 416 through a resistor 418 to energize a light 420 to indicate that the synchronizer circuit has been enabled.

The amplified R-wave from the preamplifier 402 is applied to the base of a transistor 422 through a resistor 424, a diode 426 and a capacitor 430. In addition, the R-wave is applied to a transistor 432 through a transistor 434. The transistor 432 serves to invert the polarity of the R-wave and applies the inverted polarity to the transistor 422 through a diode 434 and a capacitor 436. Hence, an R-wave of either polarity can render the transistor 422 conductive to thereby render the transistor 414 nonconductive and permit the capacitor 58 to be discharged into the patient on the next R-wave following the closing of the switches 32 and 34. Following the discharge, the defibrillate relay triggering pulse from the transistor 332 is coupled to the integrated circuit 408 via a resistor 438 and a capacitor 440 in the pulse shaping network 348 and a limiting resistor 442. This serves to reset the integrated circuit 408, and to disable the synchronizing circuit 400 in order to permit the defibrillator 10 to be discharged at will unless the switch 406 is again momentarily depressed.

The defibrillator according to the invention employs many safety features for preventing injury to the patient and damage to the unit. For example, circuitry is employed to prevent the capacitor 58 from being discharged while the unit is charging. The circuitry employs a diode 444 to clamp the output of the oscillator 282 to the gate 264 of the bistable multivibrator 260. Since the gate 264 is low when the unit is charging, the diode 444 clamps the junction of the resistor 326 and the capacitor 328 to a low potential, thereby preventing the high potential from the transistor 298 from initiating the defibrillating cycle as long as the unit is charging.

In order to prevent a patient from accidentally being given too large a defibrillation charge, such as can occur if a high energy setting is first selected by the selector switch 36 and then it is decided to administer a lower energy charge, a switch 443 ganged to switch 36 is used momentarily to interrupt the power applied to the logic circuitry 54 each time the setting of switch 36 is changed. This causes the coil 378 of the disarming relay 364 to be momentarily deenergized, thereby momentarily closing the contact 382 and discharging the capacitor 58.

To provide an additional measure of safety, the multivibrators 226 and 260 are powered by the output of the multivibrator 362 so that they cannot be accidentally toggled to start the charging cycle unless the charge switch 38 is closed. In addition, a diode 446 and a resistor 448 couple the output of the monostable multivibrator 284 to the driver transistor 366 to assure that the disarming relay 64 is maintained energized during the entire discharge cycle. The output of the monostable multivibrator 284 is also used to reset the bistable multivibrator 226 to terminate the energization of the ready light 246 and the loud speaker 248.

When a flyback type of power supply is used to charge a capacitor, the capacitor can become excessively charged if the circuitry controlling the flyback power supply should fail to turn off the flyback power supply as required. Accordingly, a pair of sensing circuits 450 and 452 are employed to sense such a condition. The circuit 450 employs a transistor 454 that is coupled to an output of the bistable multivibrator 260 through a diode 456 and a resistor 458. The transistor 454 is rendered conductive by the bistable multivibrator 260 only when the bistable multivibrator 260 is in a state corresponding to a charging condition. This prevents the pulses occurring across the transistors 146 and 148 from being transferred through the network comprising a diode 460, a capacitor 462 and a resistor 464 to the bistable multivibrator 362. If the condition of the bistable multivibrator 260 is other than that corresponding to a charging condition, the transistor 454 is rendered nonconductive. If under this condition pulses are present across the transistors 146 and 148 indicating that the supply is operating, these pulses are passed through the diode 460, capacitor 462 and resistor 464 to the bistable 362. This causes the disarming relay 64 to be deenergized and dumps the charge accumulated on the capacitor 58 in order to prevent the capacitor 58 from being over charged. The circuit 452 prevents the capacitor 58 from being charged to too high a level by sensing the amplitude of the voltage spikes across the transistors 146 and 148, since there are an indication of the charge on the capacitor 58. The pulses appearing across the transistors 146 and 148 are applied to the emitter of a transistor 466, connected in a common base configuration, through a diode 468, a resistor 470 and a Zener diode 472. If the amplitude of the pulses across the transistors 146 and 148 reaches a sufficient level to break down the Zener 472, the transistor 466 is rendered conductive and applies a positive signal to the gate 372 of the bistable multivibrator 362 via a diode 474. This renders the bistable multivibrator 362 operative to cause the disarming relay 378 to dump the charge accumulated on the capacitor 58 in the manner previously described.

A low battery logic circuit 476 comprising a pair of transistors 478 and 480 and a Zener diode 482 senses the voltage across the battery 56. As long as the voltage of the battery 56 is sufficiently high to maintain the Zener diode 482 in a break-down condition, the transistor 480 is rendered conductive and the transistor 478 rendered nonconductive, thereby maintaining the low battery light 44 nonenergized. If the battery voltage falls below that level required to break down the Zener diode 482, the transistor 480 is rendered nonconductive, and renders the transistor 478 conductive to complete the circuit through the low battery light 44 through a current limiting resistor 484.

Figure 5:
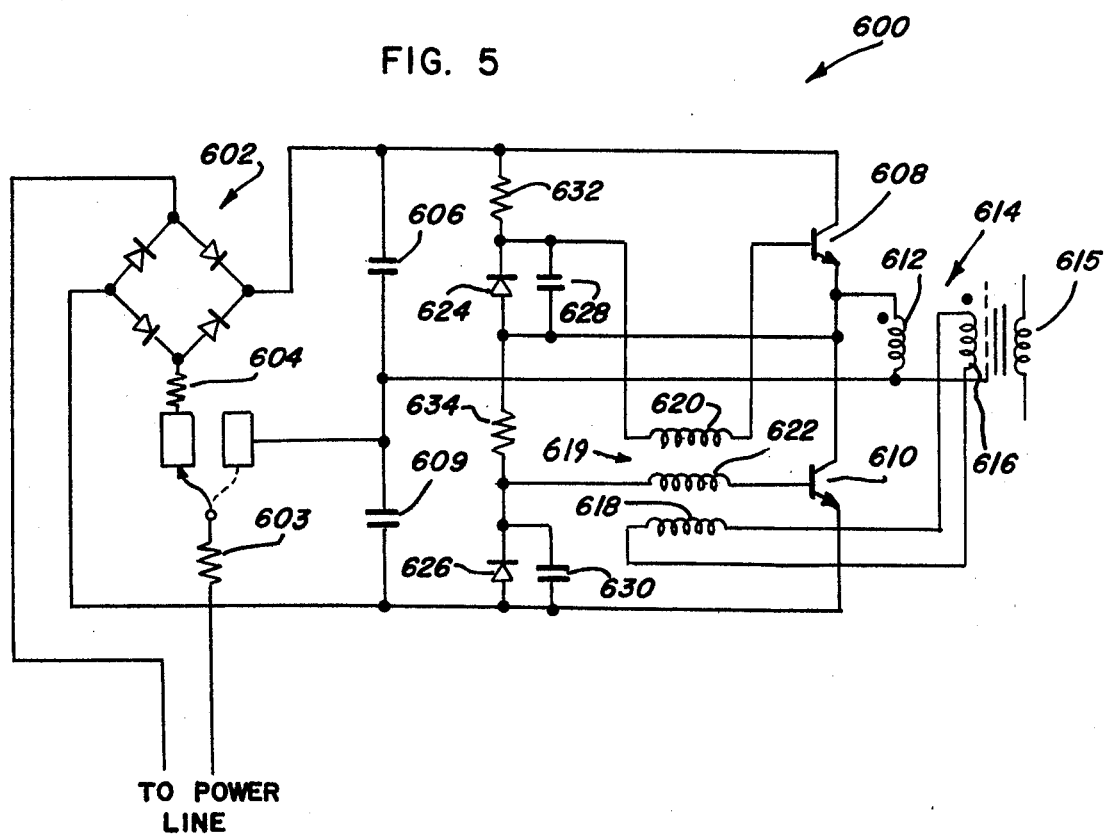
FIG. 5 is a schematic diagram of an alternative embodiment of a switching power supply usable in place of the switching power supply illustrated in FIG. 4.
Figure 2:
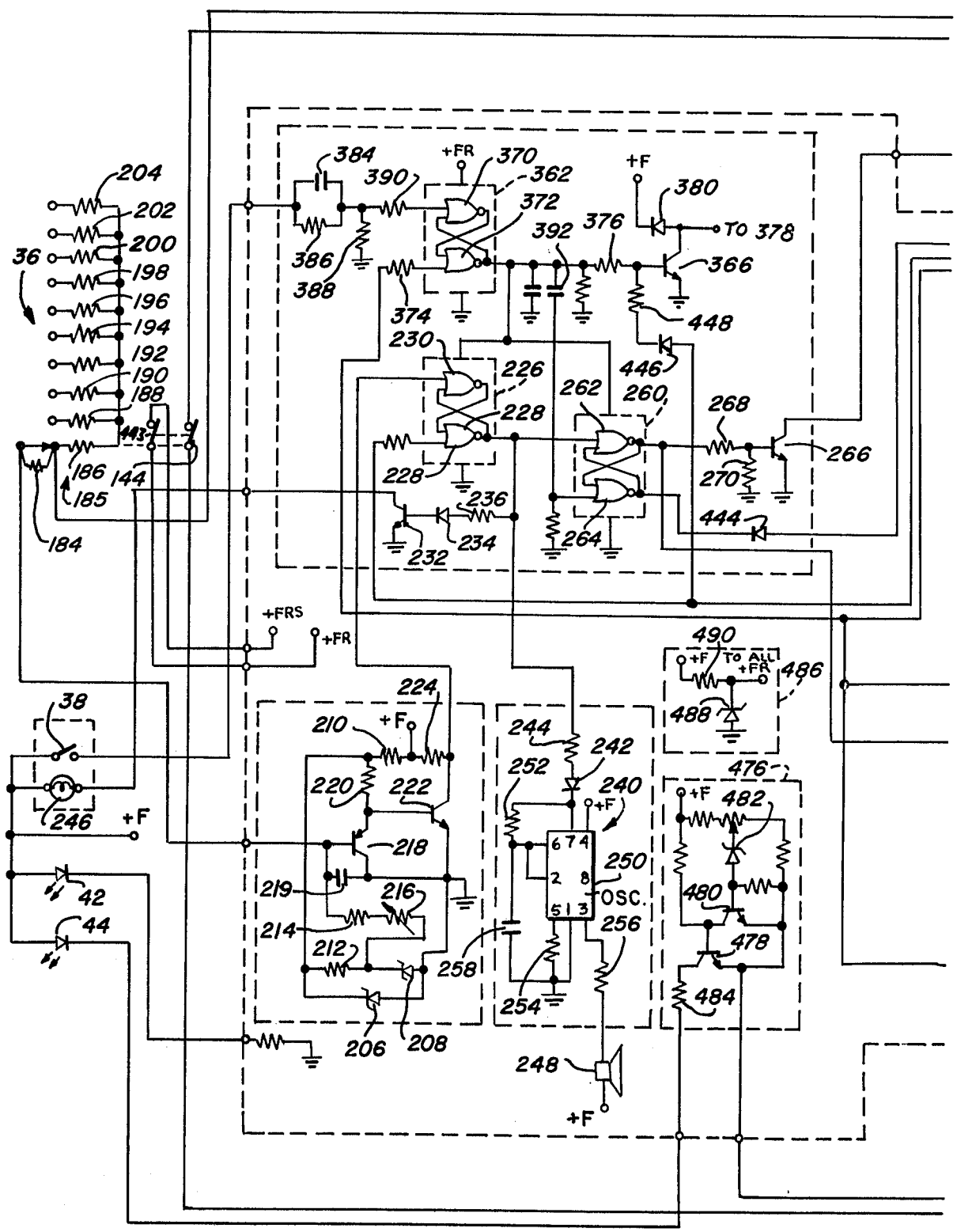
FIGS. 2-4 form a detailed electrical schematic diagram of the defibrillator according to the invention.

FIG. 5 shows an alternative embodiment of a switching power supply that may be used in place of the power supply 50. The power supply, generally designated by the reference numeral 600 in FIG. 5 utilizes a bridge rectifier 602 similar to the rectifier 64 in the power supply 50. The bridge rectifier 602 is connectable to a 240 volt source of power through a pair of resistors 603 and 604, and operates as a full wave bridge rectifier. Alternatively, if a 120 volt source of power is available, one line of the power source is connected to the center tap of a pair of capacitors 606 and 609 and the rectifier 602 serves as center tapped positive and negative power source.

In accordance with an important feature of the present invention the power source 600 uses a pair of switching transistors 608 and 610 for alternatively connecting a primary winding 612 of a transformer 614 to either a positive source of potential or a negative source of potential with respect to the center tap of the capacitors 606 and 608. This alternating current applied to the winding 612 is transformed to the appropriate voltage level to operate the defibrillator circuitry by a secondary winding 615 analogous to the winding 102 of the power supply 50. A feedback winding 616 drives a primary winding 618 of a second transformer 619 that provides feedback to the transistors 608 and 610 through a pair of respective secondary windings 620 and 622 to sustain oscillation. Diodes 624 and 626 and capacitors 628 and 630 provide an emitter return for the respective transistors 608 and 610, and a pair of resistors 632 and 634 apply a forward biasing potential to the respective transistors 608 and 610. The operation of the power supply 600 is similar to that of the power supply 50 but, because one of the transistors 608 or 610 is always conductive, the transients generated in the primary winding 612 by the switching action are always conducted to ground by the conductive one of the transistors 608 and 610, and no transient eliminating circuit such as the circuit employing the diodes 136 and 138, the capacitor 140 and the resistor 142 (FIG. 4) are necessary, thereby simplifying the construction of the power supply. The frequency of operation of the power supply 600 can be conveniently adjusted by altering the parameters of the transformer 619. Also, the transformer 619 may be designed to saturate before the transformer 614 saturates to provide the same advantages as are provided by the saturable reactor so utilized in the power supply 50 of FIG. 4.

The functions of several minor components of the circuit were not discussed for reasons of simplicity, since these components are either standard biasing resistors, or bypass capacitors for bypassing the transients resulting from the various high power circuits to ground. In addition, a standard regulator circuit 486 comprising a Zener diode 488 and a resistor 490 was not discussed, since this is a standard regulator circuit used in many prior art applications, and serves only to provide a stabilized power supply to the various components.

Obviously, many modifications and variations of the present invention are possible in light of the above teachings. Thus, it is to be understood that, within the scope of the appended claims, the invention may be practiced otherwise than as specifically described above.

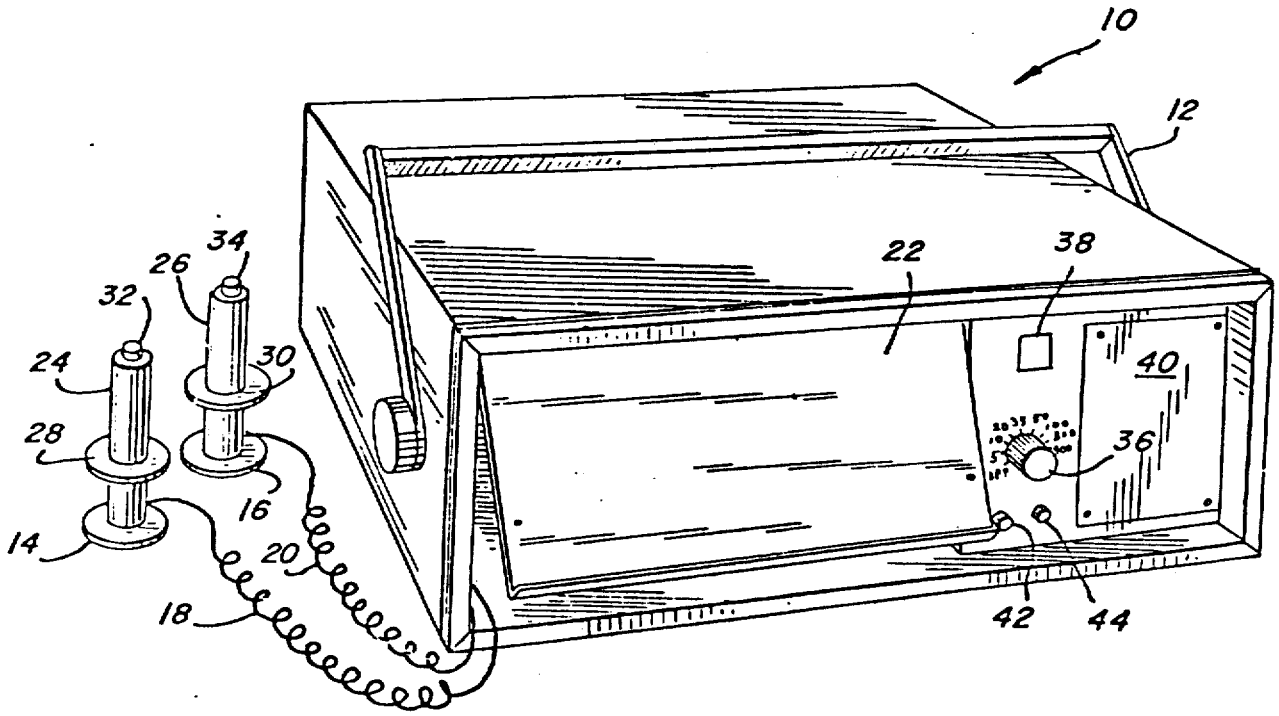

What is claimed and desired to be secured by Letters Patent of the United States is:

1. A defibrillator unit for applying a controlled electrical shock to a patient comprising:
    means including a pair of electrodes for making electrical contact to the patient;
    a storage capacitor;
    means for selectively connecting said storage capacitor to said electrodes;
    a flyback type power supply having a transformer including a main winding and a high voltage winding, and switching means connected to said main winding for periodically applying a gradually increasing current to said main winding and abruptly interrupting the flow of current through said main winding when the current therethrough reaches a predetermined level, said high voltage winding providing high voltage pulses in response to the interruptions of the current through said main winding;

means for rectifying said high voltage pulses;

means electrically connecting said rectifying means and said storage capacitor to permit said storage capacitor to be charged by said power supply; and means for determining the level to which said storage capacitor is to be charged including means for sensing the amplitude of said high voltage pulses and means responsive to said level determining means and said sensing means for terminating the charging of said capacitor when said selected level is reached.

2. A defibrillator as recited in claim 1 wherein said high voltage winding is direct current isolated from said power supply and said electrical connecting means includes a direct current connection between said rectifying means and said storage capacitor.

3. A defibrillator as recited in claim 2 wherein said selective connecting means includes a double-pole, double-throw relay, each pole having an armature, a normally closed contact and a normally open contact, each said armature normally being in contact with said respective normally closed contacts and switchable for contacting said normally open contact upon energization of said relay, said capacitor having first and second terminals, wherein said one of said normally open contacts is connected to each of said terminals, and one of said electrodes is connected to each of said armatures.

4. A defibrillator as recited in claim 3 further including means including a preamplifier having first and second input terminals each connected to one of said normally closed contacts for amplifying electrical signals received from said electrodes for operating the defibrillator in synchronism therewith.

5. A defibrillator as recited in claim 1 wherein said determining means includes variable means for altering the level to which said storage capacitor is to be charged.

6. A defibrillator unit as recited in claim 5 further including means responsive to said level altering means for discharging said capacitor when a change is made in the level selected by said level selecting means.

7. A defibrillator unit as recited in claim 6 wherein said level selecting means includes a level selector switch having a plurality of settings, and wherein said discharging means includes a second switch mechanically coupled to said selector switch, said second switch being operable by said selector switch whenever the setting of said selector switch is changed.

8. A defibrillator as recited in claim 1 wherein said sensing means includes a winding of said transformer providing reduced amplitude pulses proportional in amplitude to said high voltage pulses.

9. A defibrillator as recited in claim 8 wherein said winding is a feedback winding of said flyback type power supply.

10. A defibrillator as recited in claim 8 wherein said selecting means includes a plurality of resistors connected to said winding and means including a selector switch connected to said charging terminating means for selectively connecting one of said resistors to said charging terminating means.

11. A defibrillator as recited in claim 10 wherein said charging terminating means includes means for providing a reference current and means for comparing current produced by the pulses received from said selector switch with said reference current and terminating said charging when the amplitude of said pulse produced current exceeds the amplitude of said reference current.

12. A defibrillator as recited in claim 1 further including a load and means for discharging said capacitor into said load.

13. A defibrillator as recited in claim 12 wherein said discharging means includes a relay.

14. A defibrillator as recited in claim 13 wherein said relay includes an armature and a pair of contacts normally contacting said armature, said contacts being connected to said capacitor and said load and providing a discharge path through said armature between said load and said capacitor, said relay further including an armature energizing coil, said armature being responsive to the energization of said coil for opening the circuit between said contacts.

15. A defibrillator as recited in claim 14 wherein said defibrillator includes logic means for energizing said coil when said storage capacitor is being charged by said flyback type power supply.

16. A defibrillator as recited in claim 15 wherein said logic means includes means for automatically deenergizing said coil a predetermined time after said capacitor is connected to said electrodes by said selective connecting means.

17. A defibrillator as recited in claim 16 further including means for terminating the operation of the flyback power supply, said flyback power supply being responsive to said terminating means for terminating the charging of said capacitor when the charge on said capacitor reaches a predetermined level, said defibrillator further including means for monitoring the condition of operation of said terminating means for deenergizing said coil should said power supply become nonresponsive to said terminating means.

18. A defibrillator as recited in claim 16 further including means for monitoring the amplitude of said high voltage pulses and for deenergizing said coil when the amplitude of said pulses exceeds a predetermined value.

19. A defibrillator unit as recited in claim 1 further including a main power supply electrically coupled to said flyback power supply for operating said defibrillator unit, said main power supply including a battery.

20. A defibrillator unit as recited in claim 19 wherein said main power supply includes an alternating current line operated power supply connected to said battery and operative to charge said battery.

21. A defibrillator unit as recited in claim 20 wherein said line operated power supply is a switching type power supply.

22. A defibrillator unit as recited in claim 20 wherein said line operated power supply has sufficient capacity to operate said unit even when said battery is discharged.

23. A defibrillator unit as recited in claim 1 further including a second power supply operable from a source of alternating current voltage electrically coupled to said flyback type powder supply and operative to energize said flyback type power supply, said second power supply comprising:

means for rectifying alternating current voltages to produce a direct current voltage;

means for connecting said rectifying means to said source of alternating current voltage;

a transformer having first, second and third windings;

first and second electronic switching means each having main and control electrodes, said main electrodes being coupled to said rectifying means and to said first winding, said control electrodes being electrically coupled to said second winding and receiving controls signals therefrom for alternately rendering said switching means conductive for applying said direct current voltage to said first winding;

a saturable reactor electrically coupled to said second winding for receiving current therefrom; and second rectifying means electrically coupled to said third winding for producing a direct current voltage having a predetermined polarity.

24. A defibrillator unit as recited in claim 23 wherein said saturable reactor has a predetermined saturation characteristic selected to cause said saturable reactor to saturate upon the receipt of a predetermined amount of current from said second winding, the current flowing through the windings of said transformer upon delivery of said predetermined amount of current by said second winding being insufficient to saturate said transformer.

25. A defibrillator unit as recited in claim 24 wherein said saturable reactor is connected between the control electrodes of said first and second electronic switching means.

26. A defibrillator unit as recited in claim 24 further including third rectifying means electrically coupled to said third winding, said third rectifying means being polarized to provide a direct current voltage having a polarity opposite that of the direct current voltage produced by said second rectifying means.

27. A defibrillator unit as recited in claim 1 further including a second power supply operable from a source of alternating current voltage electrically coupled to said flyback type power supply and operative to energize said flyback type power supply, said second power supply comprising:

means for rectifying alternating current voltages including positive and negative output terminals for providing positive and negative direct current voltages, respectively;

means for connecting said rectifying means to said source of alternating current voltage;

a transformer having first, second and third windings;

first electronic switching means having main electrodes and a control electrode, one of said main electrodes being connected to said positive terminal and the other of said main electrodes being connected to said first winding;

second electronic switching means having main electrodes and a control electrode, one of said main electrodes being connected to said negative terminal and the other of said main electrodes being connected to said first winding;

a second transformer having first, second and third windings, the first winding of said second transformer being connected to the second winding of said first transformer, said second and third windings of said second transformer being electrically coupled to the control electrodes of said first and second electronic switching means and applying signals thereto for alternately rendering said first and second electronic switching means conductive to alternately connect said positive and negative terminals to said first winding of said first transformer.

28. A defibrillator unit as recited in claim 27 wherein said second power supply includes second rectifying means electrically coupled to the third winding of said first transformer.

29. A defibrillator unit as recited in claim 27 wherein each of said first and second electronic switching means includes a switching transistor.

30. A defibrillator unit usable for applying a controlled electrical shock to a patient comprising:

means including a pair of electrodes for making electrical contact to the patient;

a storage capacitor;

means for charging said storage capacitor, said charging means including an inductor and means connected to said inductor for establishing a predetermined current flow through said inductor, said current flow establishing means including means for abruptly interrupting the flow of current through said inductor when said current flow reaches a predetermined level;

means responsive to the current flow through said inductor for generating a voltage transient upon the termination of said current flow;

means coupling said voltage transient generating means to said storage capacitor for applying said voltage transient to said capacitor to effect charging of said capacitor;

means coupled to said charging means for terminating the operation of said charging means when the charge on said capacitor reaches a predetermined level, said terminating means including means for monitoring the amplitude of the transients generated by said voltage generating means and for terminating the charging of said capacitor when the amplitude of said transients reaches a predetermined level; and means for selectively connecting said storage capacitor to said electrodes.

31. A defibrillator unit as recited in claim 30 wherein said voltage transient generating means includes an electrically isolated coil magnetically coupled to said inductor, means including a preamplifier having first and second inputs for providing an electrical signal representative of the R-wave of the patient for operating the defibrillator in synchronism therewith and means for selectively connecting said electrodes to said storage capacitor and to said inputs, said selective connecting means including a relay having first and second armatures and a noramlly open and a normally closed contact associated with each of said armatures, said inputs of said preamplifier being electrically connected to the normally closed contacts, and each of said electrodes being electrically connected to one of said armatures.

32. A defibrillator unit as recited in claim 30 wherein said transient amplitude monitoring means includes a coil magnetically coupled to said voltage transient generating means.

* * * * *

UNITED STATES PATENT OFFICE
CERTIFICATE OF CORRECTION

Patent No. 4,077,413  Dated March 7, 1978

Inventor(s) Leslie W. Partridge

It is certified that error appears in the above-identified patent and that said Letters Patent are hereby corrected as shown below:

The title page should be deleted and substituted with the attached therefore.

Signed and Sealed this

Fourth Day of July 1978

[SEAL]

Attest:

RUTH C. MASON
Attesting Officer

DONALD W. BANNER
Commissioner of Patents and Trademarks

United States Patent [19]

Partridge

[11] 4,077,413
[45] Mar. 7, 1978

[54] DEFIBRILLATOR

[75] Inventor: Leslie W. Partridge, Janesville, Wis.

[73] Assignee: The Burdick Corporation, Milton, Wis.

[21] Appl. No.: 683,016

[22] Filed: May 4, 1976

[51] Int. Cl.² .............................................. A61N 1/36
[52] U.S. Cl. .................................. 128/419 D; 363/37
[58] Field of Search .................. 128/419 D, 421, 422, 128/423; 331/112, 148; 321/2

[56] References Cited

U.S. PATENT DOCUMENTS

| 3,258,013 | 6/1966 | Druz | 128/419 D |
| 3,389,704 | 6/1968 | Buchowski et al. | 128/419 D |
| 3,513,850 | 5/1970 | Weber | 128/419 D X |
| 3,547,108 | 12/1970 | Seiffert | 128/419 D X |
| 3,653,387 | 4/1972 | Ceier | 128/419 D X |
| 3,814,105 | 6/1974 | Howard et al. | 128/419 D |
| 3,828,239 | 8/1974 | Nagai et al. | 321/2 |
| 3,860,009 | 1/1975 | Bell et al. | 128/419 D |
| 3,863,125 | 1/1975 | Tollrian et al. | 321/2 X |
| 3,925,717 | 12/1975 | Kinnard | 321/2 |

FOREIGN PATENT DOCUMENTS 864,362    4/1961    United Kingdom ............ 128/419 D Primary Examiner—William E. Kamm
Attorney, Agent, or Firm—Mason, Kolehmainen, Rathburn & Wyss

[57] ABSTRACT

An improved automatic defibrillator operable from an internal rechargable battery power source or from an A.C. line when the battery is discharged utilizes a high efficiency flyback type power supply for charging the energy storage capacitor. The capacitor charging power supply employs an isolated output thereby allowing the defibrillator electrodes to be switched between the storage capacitor and an electrocardiogram unit by the discharge relay and avoiding the need for a separate relay or isolating impedance to isolate the preamplifier of the electrocardiogram unit from the defibrillator circuit. Finally automatic circuitry is employed to control the battery power supply so that the number of watt seconds (Joules) of energy delivered by the defibrillator may be easily selected by a single selector switch, and the charging of the capacitor terminated when the energy necessary to deliver the amount of energy selected has been stored.

32 Claims, 5 Drawing Figures